United States Patent
Yang et al.

(10) Patent No.: US 7,047,235 B2
(45) Date of Patent: May 16, 2006

(54) METHOD AND APPARATUS FOR CREATING MEDICAL TEACHING FILES FROM IMAGE ARCHIVES

(75) Inventors: Guo Liang Yang, Singapore (SG);
Wieslaw L. Nowinski, Singapore (SG);
Choie Cheio Tchoyoson Lim,
Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 463 days.

(21) Appl. No.: 10/307,190

(22) Filed: Nov. 29, 2002

(65) Prior Publication Data

US 2004/0107210 A1    Jun. 3, 2004

(51) Int. Cl.
*G06F 17/30* (2006.01)

(52) U.S. Cl. .............................. 707/3; 707/4; 707/100; 707/101; 707/102; 707/103 R; 707/104.1

(58) Field of Classification Search ................ 707/3, 707/4, 100, 101, 102, 103 R, 104.1; 705/2, 705/3; 600/408, 437; 709/202, 203; 365/52
See application file for complete search history.

(56) References Cited

U.S. PATENT DOCUMENTS

| | | | | |
|---|---|---|---|---|
| 5,592,408 A * | 1/1997 | Keskin et al. ................ 365/52 |
| 5,622,171 A * | 4/1997 | Asada et al. ................ 600/408 |
| 5,699,038 A * | 12/1997 | Ulrich et al. .......... 340/286.07 |
| 5,715,823 A * | 2/1998 | Wood et al. ................ 600/437 |
| 5,867,821 A * | 2/1999 | Ballantyne et al. ............ 705/2 |
| 5,884,246 A * | 3/1999 | Boucher et al. ............... 704/2 |
| 5,903,889 A * | 5/1999 | de la Huerga et al. .......... 707/3 |
| 5,918,010 A * | 6/1999 | Appleman et al. .......... 709/203 |
| 6,012,083 A * | 1/2000 | Savitzky et al. ............ 709/202 |
| 6,018,713 A * | 1/2000 | Coli et al. ..................... 705/2 |
| 6,263,330 B1 * | 7/2001 | Bessette ........................ 707/4 |
| 2003/0208477 A1 * | 11/2003 | Smirniotopoulos et al. ..... 707/3 |
| 2003/0225597 A1 * | 12/2003 | Levine .......................... 705/3 |

* cited by examiner

Primary Examiner—Frantz Coby
(74) Attorney, Agent, or Firm—Seed IP Law Group PLLC

(57) ABSTRACT

A method for retrieving medical images from at least one image archive and creating at least one teaching file; the method including the steps of retrieving at least one medical image from the image archive; storing the at least one medical image in a database; generating a database record for the teaching file; generating the teaching file; saving the teaching file into the database; and generating at least one index of the teaching file.

35 Claims, 8 Drawing Sheets

METHOD AND APPARATUS FOR CREATING MEDICAL TEACHING FILES FROM IMAGE ARCHIVES

FILED OF THE INVENTION

The present invention relates to a method and apparatus for creating medical teaching files from image archives and refers particularly, though not exclusively, for use of such a method and apparatus for radiological teaching and information exchange using images retrieved from clinical archives.

ABBREVIATIONS AND ACRONYMS

Throughout this specification the following abbreviations and acronyms shall have the following meanings:
ACR: American College of Radiology;
DICOM: Digital Imaging and Communications in Medicine. This is a standard medical imaging format and protocol;
GUI: Graphical User Interface;
HTTP: HyperText Transfer Protocol. This is an application-level protocol for distributed, collaborative, hypermedia information systems;
ID: Identifier. An identifier is a string used to identify a patient, or a study, in the DICOM protocol;
JPEG: Joint Photographic Experts Group. This is a popular image format (usually with file extension .jpg or jpeg);
MIRC: Medical Imaging Resource Center. This is a distributed medical imaging library and standard defined by RSNA. For the definition of RSNA see below,
MIRIP: Medical Imaging Repository Interfacing with PACS. For the definition of PACS, see below. MIRIP is the name of the system utilizing the method and apparatus of the present invention;
PACS: Picture Archiving and Communication System. The clinical image archive system;
RSNA: Radiological Society of North America;
TF: Teaching File, which is a document containing text and images that is useful for medical education;
UID: Unique Identifier, which is a number that uniquely identifies an object in the DICOM standard; and
XML: Extensible Markup Language as defined by the World Wide Web Consortium (W3C), to make it easy and straightforward to use on the Web: easy to define document types, easy to author and manage documents, and easy to transmit and share across the Web

BACKGROUND TO THE INVENTION

Medical (e.g. radiological) images are important building blocks for clinical support, teaching and research. In digital environments such as PACS, images may be manipulated and cross-referenced in a powerful and interactive fashion. As more hospitals adopt PACS, a scalable repository of case-based files will become a valuable tool for on-demand learning and exchange of data. However, a solution does not yet exist to interface such a repository with a clinical PACS. MIRC, which was developed in 2001 under the leadership of RSNA, is a standardized platform for exchanging image data.

No vendor of PACS systems presently provides a solution for creation of medical teaching files as a commercial option. Many teaching hospitals and universities have designed in-house solutions using a variety of formats. Recently, the RSNA has defined standards for MRIC. MIRC has the potential to be a worldwide set of standards defining teaching file and research data sets in the same fashion as DICOM has become the de facto standard for PACS.

Systems that can retrieve medical images and other information from PACS to compose radiological teaching files in a teaching file library, and share with other teaching file libraries using the MIRC protocols are not yet available.

It is therefore the principal object of this present invention to provide a method and apparatus for creating teaching files from medical image archives.

SUMMARY OF THE INVENTION

With the above and other objects in mind, the present invention provides a method for retrieving medical images from at least one imaging archive and creating at least one teaching file; the method including the steps of retrieving at least one medical image from the at least one image archive; storing the at least one medical image in a database; generating a database record for the at least one teaching file; generating the teaching file; saving the teaching file into the database; and generating at least one index of the teaching files.

A searching mechanism for searching the teaching file may be provided; and when the at least one medical image is retrieved from the at least one clinical database, patient specific information related to the at least one medical image may be retrieved with the at least one medical image. The patient specific information may include sensitive information, the sensitive information being subjected to an anonymization process; the anonymization process preferably including replacing each item of the sensitive information with an anonymization code. The anonymization code may include a randomly generated number, a prefix and a type. The prefix may be a short string of characters representing the creator of the sensitive information; and the type may represent a nature of the sensitive information.

A check may be first performed to determine if the item of sensitive information has previously been anonymized and the anonymization code previously generated; and, if yes, retrieving and using the previously generated anonymization code.

The sensitive information may include one or more of: patient's name, patient ID, other patient's names, other patient IDs, patient's birth name, patient's address, patient's telephone numbers, patient's mother's birth name, region of residence, country of residence, military rank, branch of service, patient comments, additional patient history, referring physician's name, referring physician's address, referring physician's telephone numbers, and all other person names.

Retrieval of the at least one medical image may be in batches or interactively. When retrieval is in batches, a plurality of medical images and information relative to the plurality of medical images is retrieved automatically using groups of patient identifiers or groups of study identifiers. The retrieval may be by a PACS accessor of an image server reading and retrieving the plurality of medical images from the at least one clinical image archive according to the patient identifiers or the study identifiers.

When the retrieval is interactive, the at least one clinical image archive may be queried using a graphic user interface and instructions are passed from the graphic user interface to a PACS accessor of an image server, the PACS accessor interrogating the at least one clinical image archive, finds at least one medical image of interest, and retrieving the at least one medical image and information relative to the at least one medical images.

The at least one medical image may be received from the at least one clinical image archive, the image server then first storing the image in a temporary disk directory and validating the at least one image according to a DICOM standard; and, if the at least one image is not a valid DICOM image, the image server may discard the at least one image and check in the database for duplication.

If the at least one image already exists in the database, the image server may move the at least one image into a duplication directory. If the at least one image is not in the database, the image server preferably queries the at least one clinical image archive to retrieve relevant patient, study, series and image information, and merge the information with the at least one medical image; and store the information and the at least one medical image in the database.

The at least one medical image and information are preferably stored in the database and indexed by one or more of patient's name, patient ID, study ID, series ID and image ID.

The at least one medical image may be spanned to multiple storage media by determining when a current storage medium reaches its maximum capacity, finding a further storage medium with sufficient free space, and sending further medical images for storage to the further storage medium.

The present invention also provides apparatus for retrieving medical images from at least one image archive and creating at least one teaching file: the apparatus including a database, an image server, a MIRC server, a web server, and a graphic user interface for operation on a user's machine.

The database may be a relational database for storage of all required information, including database tables, database indexes, database scripts, and pointers to the medical images and teaching files The image server may be for communicating with the at least one clinical image archive, querying and retrieving the at least one medical images, and patient data, study data, series data, and image-related information from the at least one medical image.

The MIRC server preferably provides MIRC compliant functions, including MIRC queries and MIRC storage; and the web server advantageously serves requests received from a user via the graphic user interface on a user's machine, the graphic user interface being for providing access functions and MIRC file editing functions.

The image server may include a PACS accessor for querying and retrieving images from at least one image archive; a DICOM receiver for receiving the at least one medical image retrieved from the at least one image archive by the PACS accessor; and a DICOM anonymizer for anonymizing the at least one medical image received from the at least one image archive by the DICOM receiver.

An MIRIP servlet may be provided in the web server to service requests from the graphic user interface; and the graphic user interface may includes an MIRIP client as a user interface able to run in a web browser or as a stand alone application on a user's machine.

The MIRIC server may include an MIRC storage for providing an MIRC teaching file storage service for the database and for the user's machine, and an MIRC query to provide queries as defined by the MIRC scheme.

For both forms, the teaching file may be in accordance with the MIRC standard.

The present invention also provides a computer useable medium comprising a computer program code that is configured to cause a processor to execute one or more functions to perform the method described above.

DESCRIPTION OF THE DRAWINGS

In order that the present invention maybe better understood and readily put into practical effect there shall now be described by way of non-limitative example, a preferred embodiment of the present invention, the description being with reference to the accompanying illustrative drawings, in which.

DESCRIPTION OF PREFERRED EMBODIMENT

Figure 1:
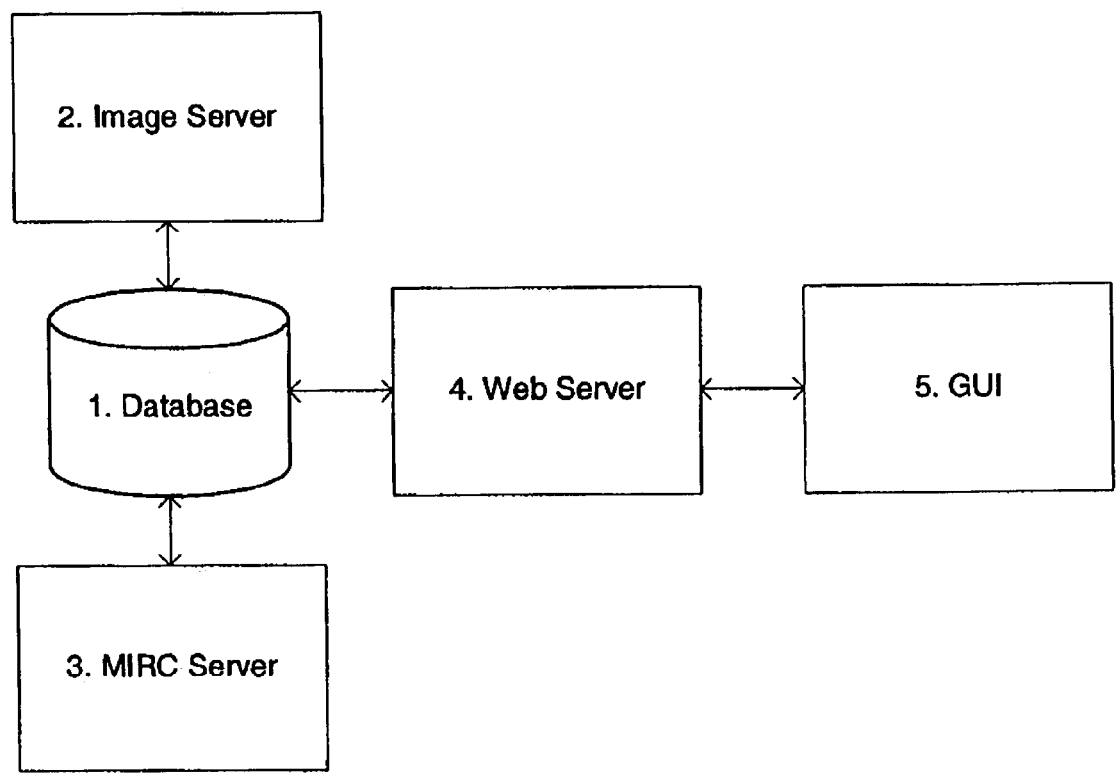
FIG. 1 is a system block diagram that illustrates the main components of the apparatus of the present invention and that are used for performing the method of the present invention.

To refer to FIG. 1, the system consists of a database 1, an image server 2, a MIRC server 3, a web server 4, and a GUI 5 operating on a user's machine.

The database 1 is a relational database It stores all information for the system, including database tables, database indexes, and database scripts. It also stores the pointers to the physical files of the system. The image server 2 communicates with the clinical image archive, queries and retrieves medical images and patient data, study data, series data, and image related information from them. The MIRC 3 server provides MIRC compliant functions, including MIRC queries and MIRC storage. The web server 4 serves various requests received from a user via the GUI 5 on a user's machine. The GUI 5 provides functions to access the system, and also provides MIRC file editing functions.

Figure 2:
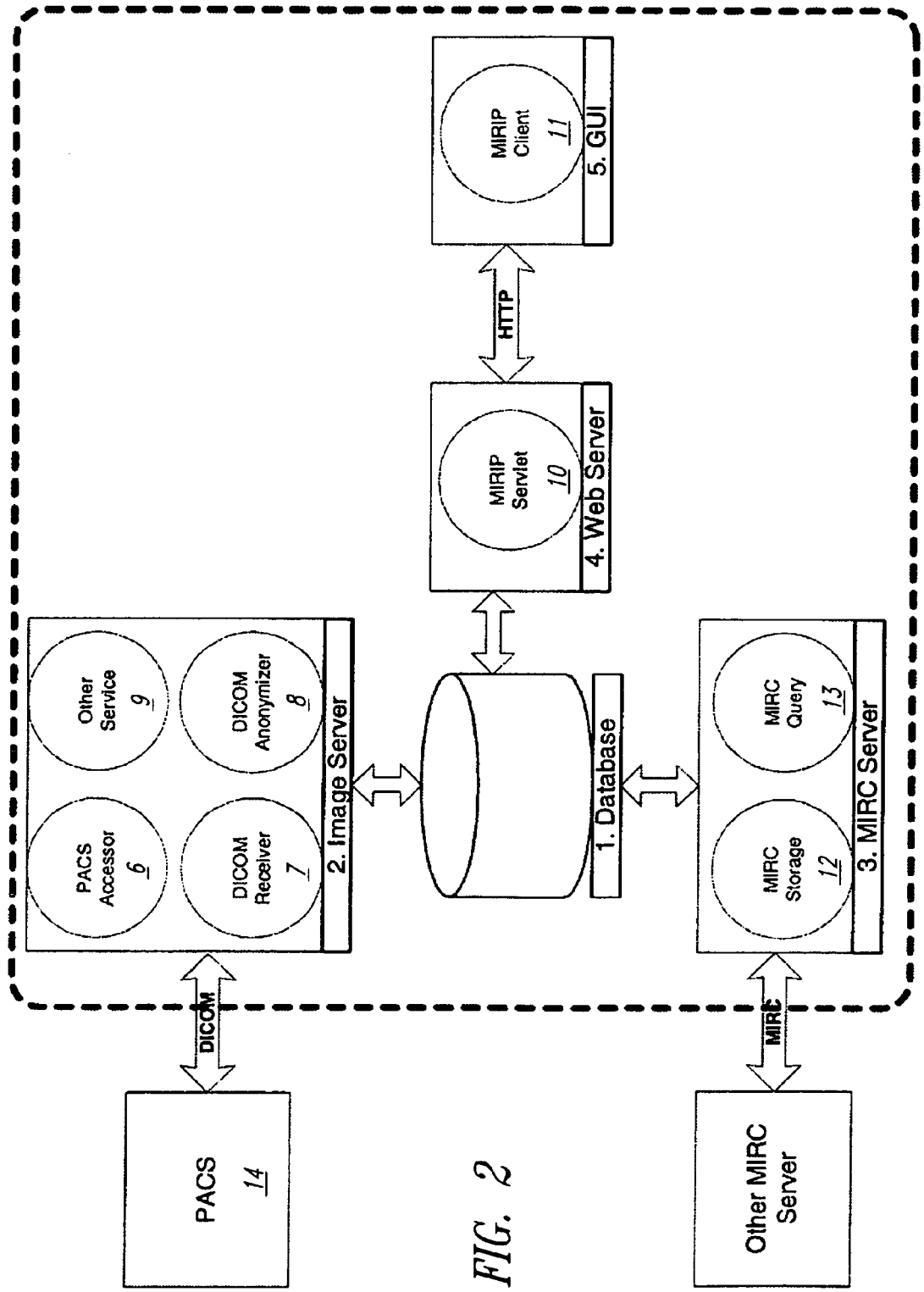
FIG. 2 is an illustration in more detail showing the components of the apparatus of FIG. 1.

A more detailed structure is illustrated in FIG. 2. Here, the image server 2 includes a PACS accessor 6 that is used to query and retrieve images from the PACS 14; a DICOM receiver 7 that is used to receive the images retrieved from the PACS 14 by the PACS accessor 6; a DICOM anonymizer 8 that is used to anonymize the images received from the PACS 14 by the DICOM receiver 7; and Other Service 9 that includes PACS Ping (Echo), and so forth.

By anonymize (and its grammatical equivalents) it is meant that predetermined identification details of the patient, study, and so forth, are made anonymous so that a reader cannot determine the identity of the patient study, or the like.

An MIRIP servlet 10 runs in the web server 4 to service requests from the GUI 5, and MIRIP client 11 is a user interface that can be run in a web browser or as a stand alone application on the user's machine.

MIRC storage 12 is part of the MIRC server 3 and provides an MIRC teaching file storage service for the database 1 and for a user's machine. MIRC query 13 is also part of the MIRC server 3 and provides queries as defined by the MIRC scheme.

Figure 3:
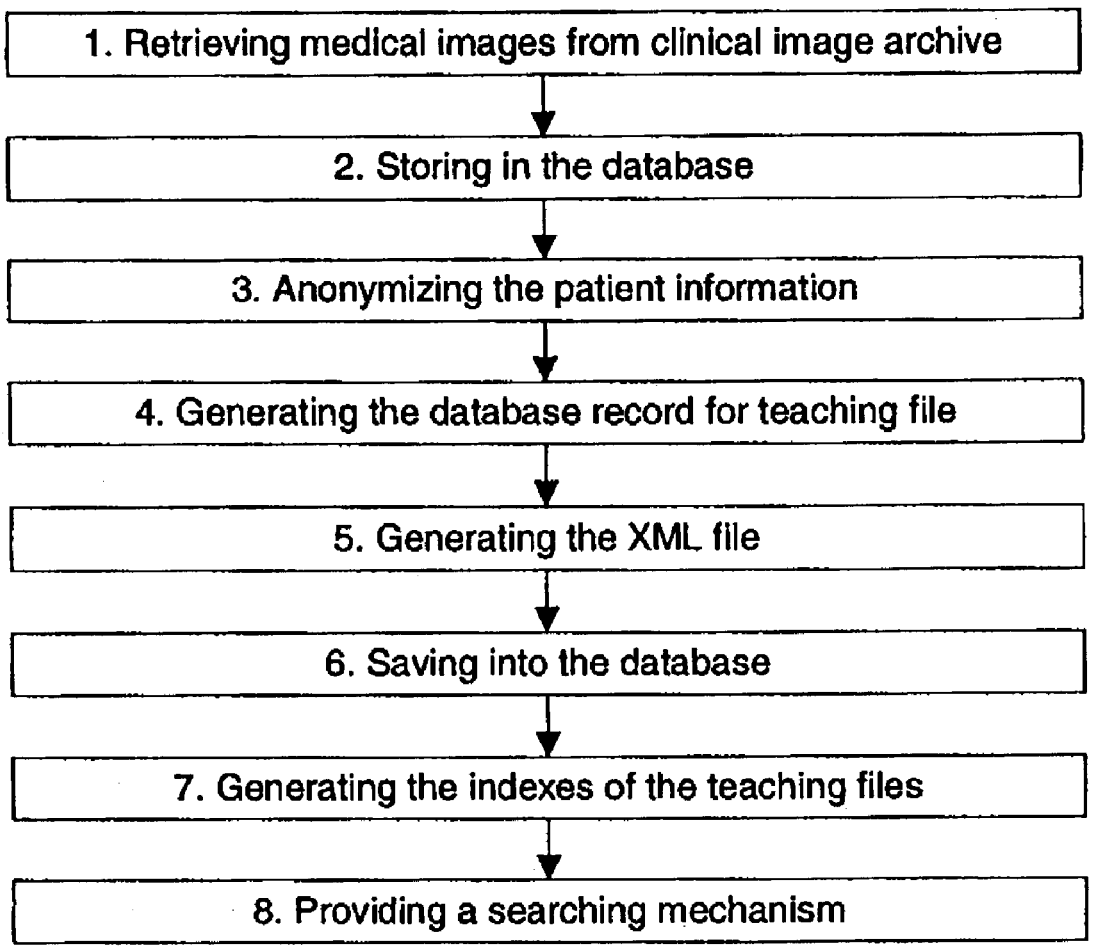
FIG. 3 is a system flowchart that illustrates the principal steps to create teaching files from clinical image archives.

The method is illustrated in FIG. 3 and includes the steps:
1. retrieving medical images from the clinical image archive 14;
2. storing the retrieved medical images in the database 1;
3. anonymizing the patient information so that the user cannot obtain the patient information;
4. generating the database record for the teaching file;
5. generating the XML file;
6. saving the XML file into the database 1;
7. generating the indexes of the teaching files; and
8. providing a searching mechanism.

Figure 4:
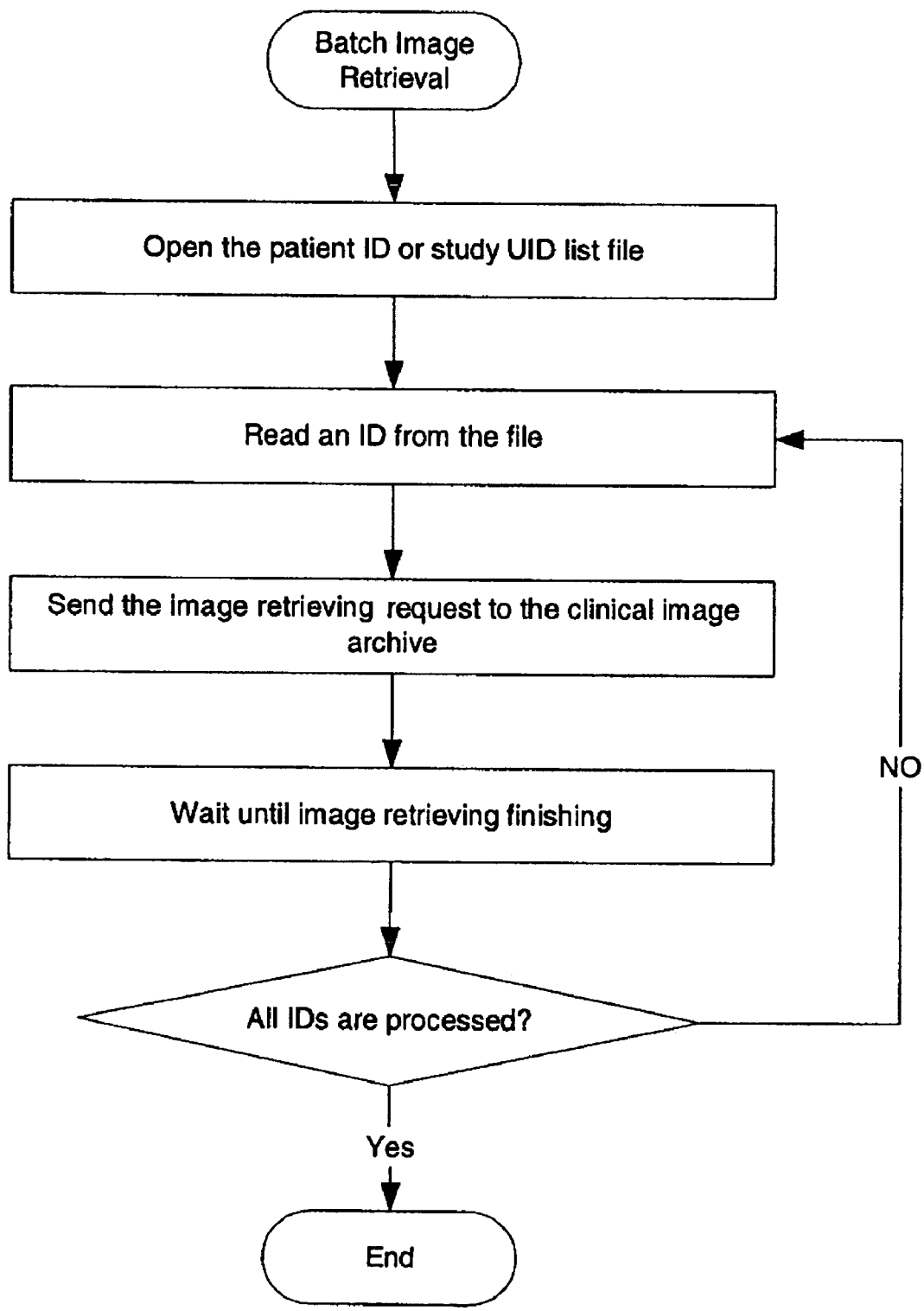
FIG. 4 is a flowchart of the batch image retrieval process as part of the first step of FIG. 3 and illustrates the steps required to retrieve medical images from the clinical image archive.

FIG. 4 illustrates the first step (1) of the method—retrieving medical images from the clinical image archive. The radiology department of a hospital generates a large number of medical images every day. Most images are in digital format, and are stored in the clinical image archive—PACS. Images are generally typical or atypical. But they may be particularly suitable for generating teaching files. Clinical image archives are for clinical purposes only and use a specific communication protocol named DICOM.

The method of the present invention can interface with the clinical image archive 14; and retrieve images and patient specific information. The retrieval process itself is in accordance with the DICOM protocol. The retrieval may be in batches or interactively. When in batches, medical images and information relative to those images can be retrieved automatically using groups of patient identifiers, or study identifiers. When interactive retrieval is required, the GUI 5 is able to query the clinical image archive 14 by categories, and user-selected studies may also be retrieved.

For batch retrieval, the user provides a file containing the patient ID or the study UID. The PACS accessor 6 of the image server 2 reads the file, and retrieves the corresponding medical images from the clinical image archive 14 according to the patient IDs. In the instance of one or more studies being retrieved, the study UIDs listed are used to locate and retrieve the required images. In both instances the required patient specific information is also retrieved with each image or study, as the case may be.

When retrieval is interactive, the user queries the clinical image archive 14 through the GUI 5. Instructions are passed from the GUI 5 on the user's terminal to the PACS accessor 6. The PACS accessor 6 interrogates the clinical image archive 14, finds the patient or study of interest, and retrieves the required images. The user can also work on a diagnostics imaging workstation, using the interface provided by the workstation, and send the retrieved images to the image server 2. The process ends when all IDs have been processed.

Figure 8:
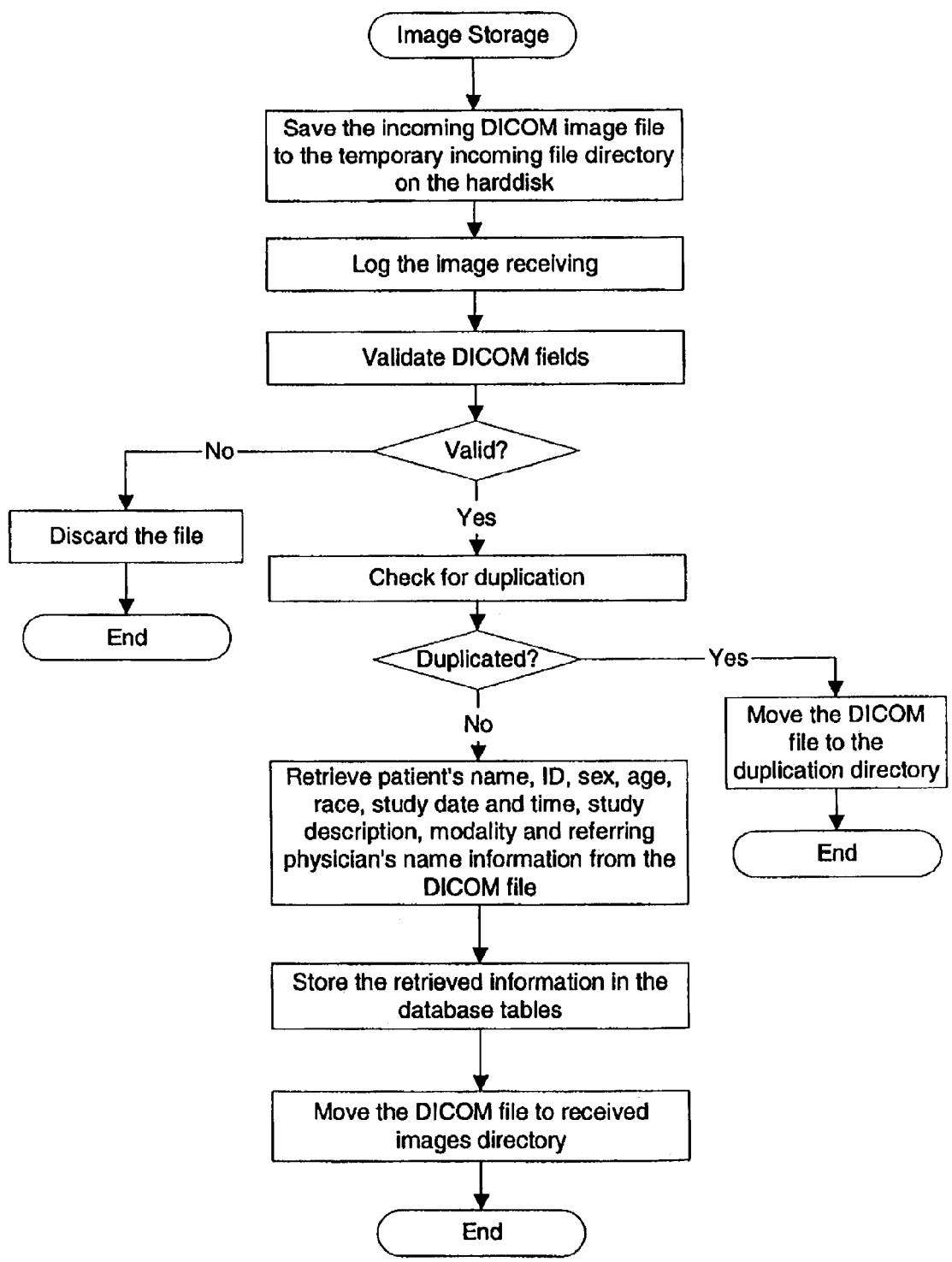
FIG. 8 is a flowchart illustrating the steps of step 2 of FIG. 3 when storing images in the database.

FIG. 8 shows the process steps involved in storing images in the database 1. When the image server 2 receives an image from the clinical image archive 14, the image server 2 first stores the image in a temporary disk directory and then validates the image according to the DICOM standard. If the image is not a valid DICOM image, it discards the image. Image server 2 then checks in the database 1 for duplication. If the image already exists in the database 1, image server 2 moves the image file into a duplication directory. If the image is not in database 1, the image server 2 queries the clinical image archive 14 to retrieve the relevant patient, study, series and image information, and merge the information with the information embedded in the incoming image file, and stores the information in the database 1.

The retrieved medical images and patient information are stored in the database 1 for further processing. Other useful information may also be extracted from the images and stored in the database. This other information may be indexed by patient's name, patient ID, study ID, series ID and image ID for the ease of searching.

Since medical images are usually large in size, they take a large amount of disk space for storage. The image can be spanned to multiple storage media. When the current storage medium reaches its maximum capacity, a storage medium with sufficient free space is found and further images for storage are sent to that storage medium.

Figure 5:
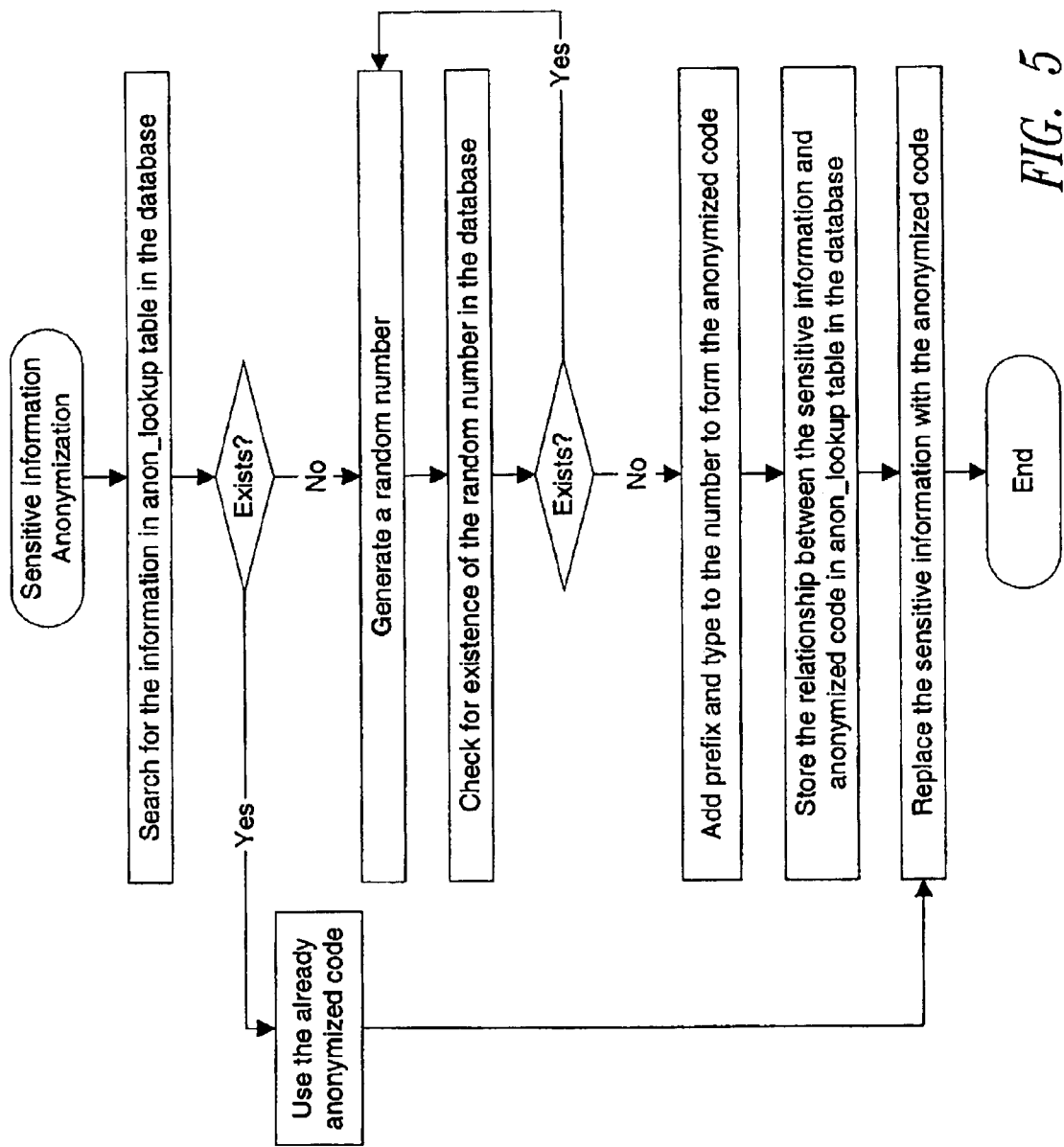
FIG. 5 is a flowchart of the third step of FIG. 3 and illustrates the steps to anonymize one item of patient sensitive information in a DICOM file.

To now refer to FIG. 5, as patient-specific information retrieved from the clinical image archive 14 is very sensitive, it can only be referenced internally. It is not allowed to appear in teaching files, which may be published. Patient sensitive information can't be simply removed from the teaching files. Sometimes it is required to refer back to the actual patient. So patient sensitive information needs to be made anonymous—or anonymized.

Whenever a whole study is received and stored in the database 1, the anonymizer 8 of image server 2 automatically starts to anonymize the images. The image server 2 keeps the correspondence relationship between the sensitive information and the anonymized code in the database 1. Image server 2 also provides a method to reveal the information before anonymization by looking up the database 1, but this method can only be used internally.

Sensitive information includes, but is not limited to, for example:
Patient's name
Patient ID
Other patient's names
Other patient IDs
Patient's birth name
Patient's address
Patient's telephone numbers
Patient's mother's birth name
Region of residence
Country of residence
Military rank
Branch of service
Patient comments
Additional patient history
Referring physician's name
Referring physician's address
Referring physician's telephone numbers
All other person names
An anonymization code may have the format of:

<Prefix> <Type>-<Number> where, prefix is usually short alphabet characters or letters, which represents the creator of the anonymized information Typically the acronym of the creating institute is used, for example, "BIL". The prefix is generated during the initial set-up of the system Type specifies the nature of the piece of anonymized information. Since patient name and ID are most frequently referenced, a "P" and a "D" may be used to represent them respectively An "X" may be used to represent all other types of information. Further classification is also possible, for example, an "A" can be used to represent address information. Again, the type is created during the initial installation of the system.

Number is a random number generated by a number generator within the anonymizer 8 in image server 2. The Number is unique and serves to distinguish the anonymized code from other codes. For example, a code, "BILP-3388", represents a patient name, is created by an organization named "BIL".

The steps illustrated in FIG. 5 are used to anonymize one item of patient sensitive information. For each item of patient sensitive information, the anonymizer 8 checks if this item of information has already been anonymized by looking up a look-up table in the records of the database 1. If yes, the already created anonymized code is used. Otherwise, anonymizer 8 generates a new random number. Anonymizer 8 then adds the prefix and type to the random number to form the anonymized code. The specific items of sensitive information are replaced with the anonymized code. The correspondence relationship between the sensitive information and the anonymized code is stored in the database 1 in a secure manner. It is normally only accessible to those having access to such information. Denial of access may be by use of one or more of known techniques including, but not limited to, a firewall, access level, passwords, PINs, members of an Intranet, and so forth.

Figure 6:
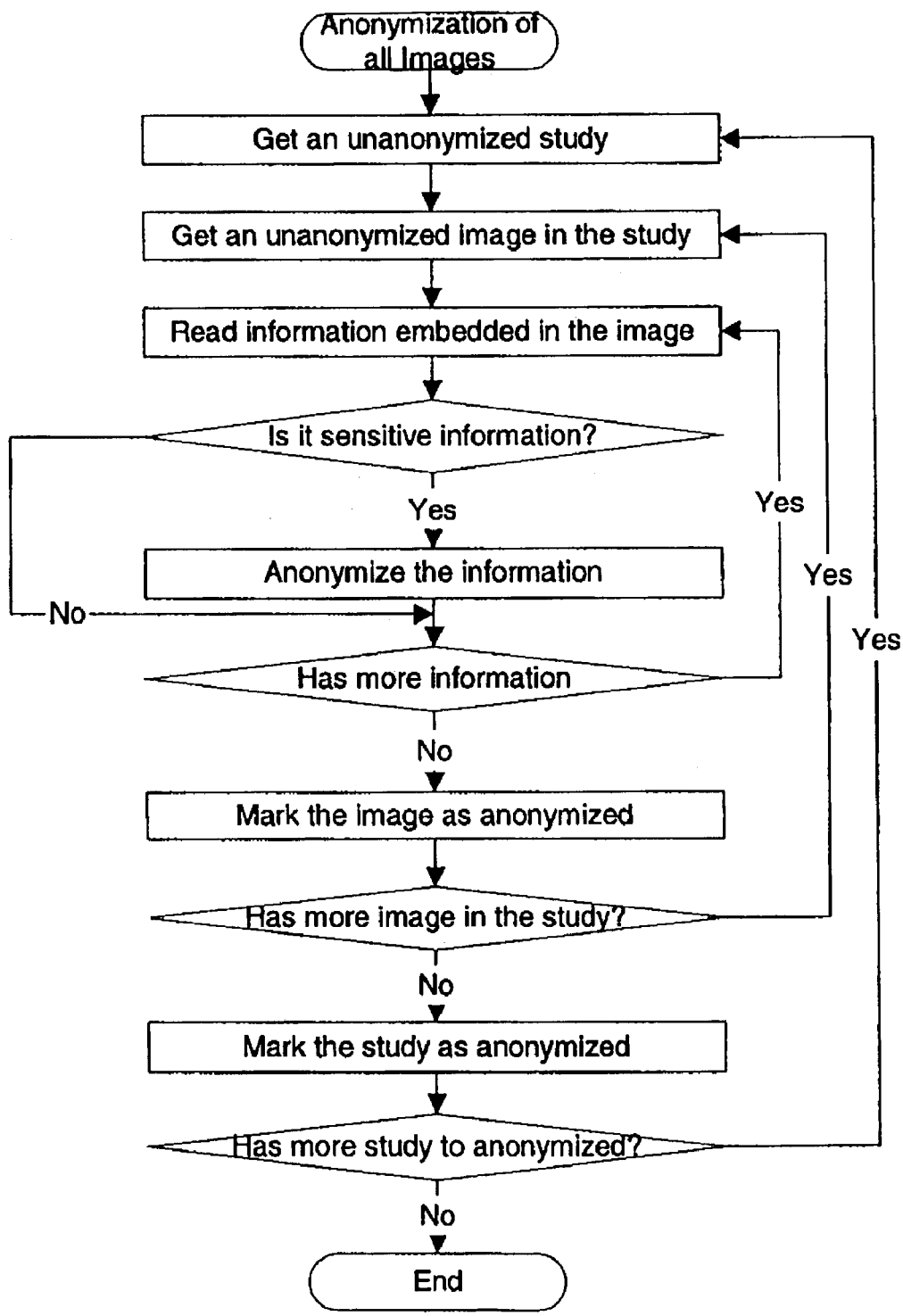
FIG. 6 is a flowchart that illustrates the steps to anonymize all DICOM files in the database.

FIG. 6 shows the steps used to anonymize all images in one or more studies or other large cluster of images. Here, after retrieval of all images, all studies that need to be anonymized are determined. The studies all processed for anonymization one-by-one. The images within each study are processed for anonymization one-by-one. For each image, all patient-sensitive information is found and anonymized using the method described above in relation to FIG. 5.

By using this anonymization method, no patient-sensitive information is disclosed to those not entitled to view the information, but the information required to be revealed to all users can be revealed to all users, and that information only able to be revealed to certain users having access to the information can be revealed to those users only.

To generate the database record for teaching file, useful information, such as patient name, ID, sex, age, race, etc, gathered from the above steps ran be used to automatically generate a teaching-file database-record.

Significant images may also be selected and inserted into the teaching file database record. They can also be deleted and re-ordered. Author information and affiliation information may be retrieved automatically from the database and then inserted into the teaching file database record.

The GUI 5 allows entry of other necessary information such as copyright information, title, difficulty level, access permission, publishing date, reviewer, abstract, keywords, clinical findings, image findings, radiological codes, diagnosis, diagnosis groups, pathology of condition, imaging of condition, differential diagnosis, similar cases, references, and so forth.

An ACR coding system may be used in the teaching file record. An ACR code has the following format:

<aaaa>.<pppp> where <aaaa> is the anatomy part, and <pppp> is the pathology part. They are digits from 0 to 9.

Figure 7:
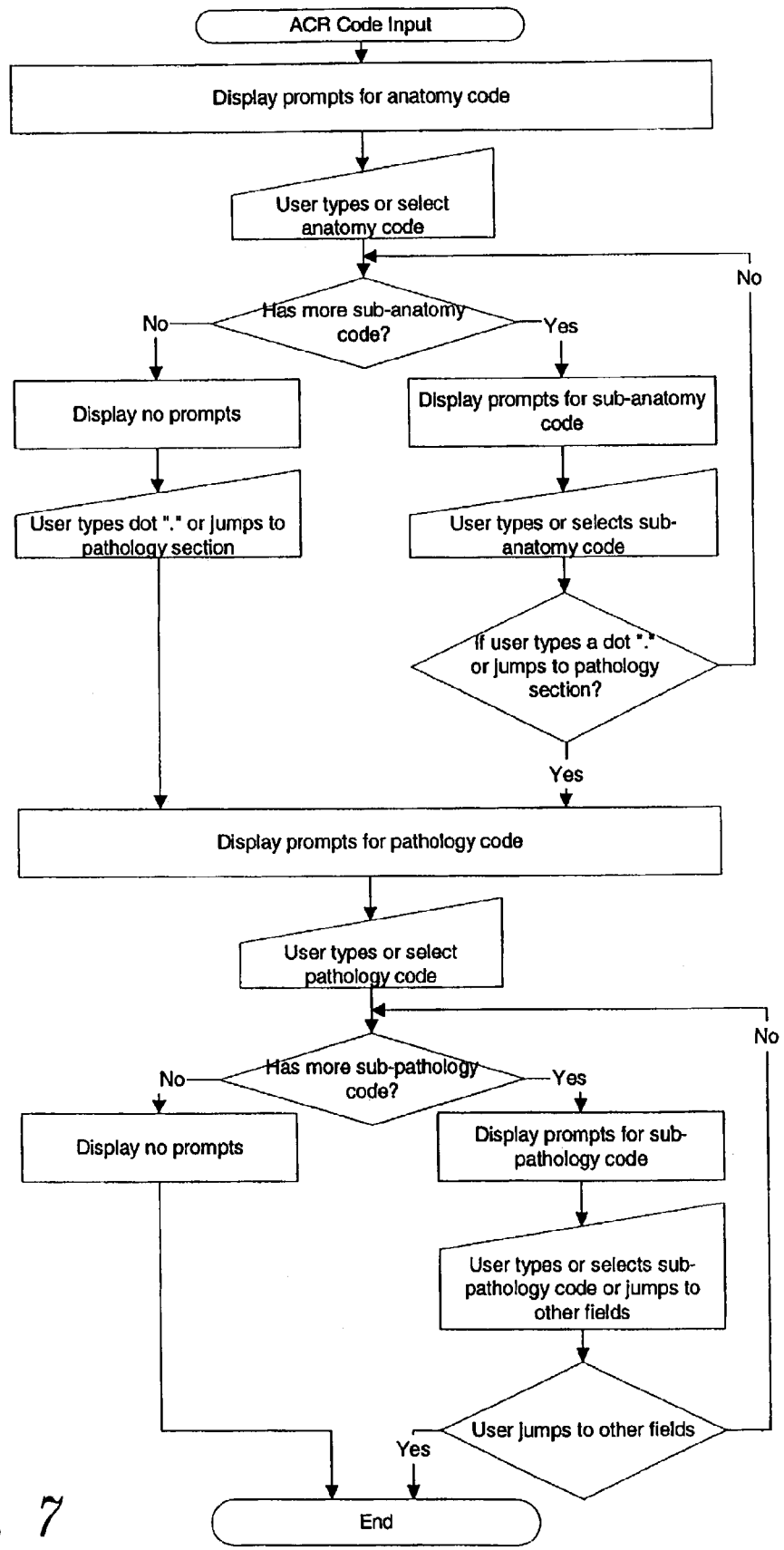
FIG. 7 is a flowchart of the steps required to interactively input an ACR code.

As shown in FIG. 7, the user is guided to input the ACR code step by step, or digit by digit. At each step, the system prompts the user with only the possible digits at the current position, and the text of corresponding meanings. As illustrated, the user inputs the anatomy codes first, and then any sub-anatomy codes. After completion of the anatomy code, the user is prompted to enter the pathology code, then sub-pathology code.

Based on the database record generated above, a teaching file complying with the MIRC scheme may be created. This may be in XML or other suitable format. The teaching file can also be previewed while editing, and it can be reloaded for modification.

An image inserted into a teaching file has two forms: a thumbnail, and a full image The images may be in JPEG format, DICOM format, or other suitable format.

The case record and the XML file together with their images (thumbnails and full images) may be stored in the database for later access. Access may include indexing, searching and retrieving.

The teaching flies stored in the database may be indexed under various categories for searching purpose. These indexes may include title, abstract, keywords, authors, affiliations, contacts, patient information, radiological codes, image format, image compression status, image modality, anatomic location, and so forth.

Internet-based searching mechanisms may be provided. There may be two types of searching mechanisms, including internal searching and external searching. Internal searching is available to those members of staff of the medical facility who have access to patient records. As such, for internal searching, patient sensitive information may be revealed. For external searching, no patient-sensitive information is revealed as it is anonymized.

Whilst there has been described in the foregoing, description a preferred embodiment of the present invention, it will be understood by those skilled in the technology that many variations or modifications in details of design, construction or operation maybe made without departing from the present invention.

The present invention extends to all features disclosed both individually and in all possible permutations and combinations.

The invention claimed is:

1. A computer-implemented method for retrieving medical images from an existing image archive and automatically creating at least one teaching file, comprising:
    retrieving at least one medical image and associated patient-specific information from the existing image archive;
    storing the retrieved medical image and associated information in a database;
    automatically generating a database record for the at least one teaching file based upon the retrieved image and associated information;
    automatically generating the at least one teaching file based upon the automatically generated database record;
    storing the generated at least one teaching file into the database; and
    generating at least one index of the stored teaching files.

2. A method as claimed in claim 1, further comprising searching the at least one teaching file using the generated index.

3. A method as claimed in claim 1 wherein the existing image archive comprises at least one clinical database.

4. A method as claimed in claim 1 wherein the associated patient-specific information includes sensitive information, and further comprising automatically anonymizing the sensitive information.

5. A method as claimed in claim 4 wherein the automatically anonymizing comprises replacing each item of the sensitive information with an anonymization code.

6. A method as claimed in claim 5 wherein the anonymization code comprises a randomly generated number, a prefix and a type.

7. A method as claimed in claim 6 wherein the prefix is a short string of characters indicating the creator of the sensitive information, and the type indicates a nature of the sensitive information.

8. A method as claimed in claim 5, further comprising:
determining if an item of sensitive information has previously been anonymized and an associated anonymization code previously generated; and,
when it is determined that the sensitive information has previously been anonymized, retrieving and using the previously generated anonymization code.

9. A method as claimed in claim 4 wherein the sensitive information includes one or more items selected from a group consisting of: patient's name, patient ID, other patient's names, other patient IDs, patient's birth name, patient's address, patient's telephone numbers, patient's mother's birth name, region of residence, country of residence, military rank, branch of service, patient comments, additional patient history, referring physician's name, referring physician's address, referring physician's telephone numbers, and all other person names.

10. A method as claimed in claim 1 wherein the retrieving of the at least one medical image is performed in batches or interactively.

11. A method as claimed in claim 10, further comprising, when the retrieving is performed in batches, automatically retrieving a plurality of medical images and associated patient-specific information using groups of patient identifiers.

12. A method as claimed in claim 10, further comprising, when the retrieving is performed in batches, automatically retrieving a plurality of medical images and associated patient-specific information using groups of study identifiers.

13. A method as claimed in claim 11 wherein the retrieving is performed by a PACS accessor of an image server by reading and retrieving the plurality of medical images from the existing image archive according to the patient identifiers.

14. A method as claimed in claim 12 wherein the retrieving is performed by a PACS accessor of an image processor by reading and retrieving the plurality of medical images from the existing image archive using the study identifiers.

15. A method as claimed in 10, further comprising:
when the retrieving is performed interactively,
querying the existing image archive using a graphic user interface; and
forwarding instructions from the graphic user interface to a PACS accessor of an image server, the PACS accessor interrogating the existing image archive, determining at least one corresponding medical image, and retrieving the determined at least one medical image.

16. A method as claimed in claim 13 wherein the retrieving of the at least one medical image further comprises:
storing the retrieved at least one medical image in a temporary disk directory;
validating the retrieved at least one medical image according to a DICOM standard;
when the retrieved at least one medical image is not a valid DICOM image, discarding the retrieved at least one medical image; and
when the retrieved at least one medical image is a valid DICOM image, checking in the database for duplication of the retrieved image.

17. A method as claimed in claim 16, further comprising when the retrieved at least one medical image already exists in the database, moving the retrieved at least one medical image into a duplication directory.

18. A method as claimed in claim 16, further comprising:
when the retrieved at least one medical image does not already exist in the database,
querying the existing image archive to retrieve associated patient, study, series and image information; and
merging and storing the retrieved information with the retrieved at least one medical image in the database.

19. A method as claimed in claim 18, further comprising indexing the stored medical image and information by one or more selected categories from a group consisting of: patient's name, patient ID, study ID, series ID and image ID.

20. A method as claimed in claim 1, further comprising spanning the retrieved at least one medical image to multiple storage media by determining when a current storage medium reaches its maximum capacity, finding a further storage medium with sufficient free spaces, and sending further medical images for storage to the further storage medium.

21. A method as claimed in claim 1, wherein the at least one teaching file is automatically generated in accordance with a Medical Imaging Resource Centre standard.

22. An apparatus for retrieving medical images from an existing image archive and automatically creating at least one teaching file, comprising:
a database;
an image server configured to retrieve at least one medical image and associated patient-specific information from the existing image archive, and to store the retrieved image and associated information in the database;
a MIRC server configured to provide access to the at least one teaching file automatically generated based upon the retrieved image and associated information;
a web server; and
a graphic user interface for operation on a user's machine.

23. Apparatus as claimed in claim 22 wherein the database is a relational database for storage of information, including database tables, database indexes, database scripts, and pointers to medical images and teaching files.

24. Apparatus as claimed in claim 22 wherein the image server is configured to communicate with the existing image archive, query and retrieve the at least one medical image and patient data, study data, series data, and image-related information associated with the at least one medical image.

25. Apparatus as claimed in claim 22 wherein the MIRC server provides MIRC compliant functions, including MIRC queries and MIRC storage.

26. Apparatus as claimed in claim 22 wherein the web server is configured to service requests received from a user via the graphic user interface; the graphic user interface configured to provide access functions and MIRC file editing functions.

27. Apparatus as claimed in claim 22 wherein the image server includes a PACS accessor for querying and retrieving images from the existing image archive.

28. Apparatus as claimed in claim 27 wherein the image server includes a DICOM receiver for receiving the at least one medical image retrieved by the PACS accessor from the existing image archive.

29. Apparatus as claimed in claim 28 wherein the image server further includes a DICOM anonymizer for automatically anonymizing the at least one medical image received by the DICOM receiver from the at least one image archive.

30. Apparatus as claimed in claim 22 wherein an MIRIP servlet is provided in the web server to service requests from the graphic user interface.

31. Apparatus as claimed in claim 22, wherein the graphic user interface includes an MIRIP client as a user interface able to run in a web browser or as a stand alone application on the user's machine.

32. Apparatus as claimed in claim 22 wherein the MIRC server includes an MIRC storage for providing an MIRC teaching file storage service for the database and for the user's machine.

33. Apparatus as claimed in claim 22 wherein the MIRC server includes an MIRC query to provide queries as defined by the MIRC scheme.

34. Apparatus as claimed in claim 22 wherein the at least one teaching file is automatically generated in accordance with a Medical Imaging Resource Centre standard.

35. A computer useable medium comprising a computer program code that, when executed, is configured to control a computer processor to retrieve medical images from an existing image archive and automatically create at least one teaching file, by performing:

retrieving at least one medical image and associated patient-specific information from the existing image archive;

storing the retrieved medical image and associated information in a database;

automatically generating a database record for the at least one teaching file based upon the retrieved image and associated information;

automatically generating the at least one teaching file based upon the automatically generated database record;

storing the generated at least one teaching file into the database; and generating at least one index of the stored teaching file.

* * * * *

UNITED STATES PATENT AND TRADEMARK OFFICE
CERTIFICATE OF CORRECTION

PATENT NO. : 7,047,235 B2 Page 1 of 1
APPLICATION NO. : 10/307190
DATED : May 16, 2006
INVENTOR(S) : Guo Liang Yang et al.

It is certified that error appears in the above-identified patent and that said Letters Patent is hereby corrected as shown below:

Title Page
Item (73) Assignee: "Agency for Science, Technology and Research, Singapore (SG)" should read as --Agency for Science, Technology and Research, Singapore (SG); National Neuroscience Institute, Singapore (SG)--

Signed and Sealed this

Nineteenth Day of February, 2008

JON W. DUDAS
*Director of the United States Patent and Trademark Office*